United States Patent
Hirata et al.

(10) Patent No.: US 10,061,218 B2
(45) Date of Patent: Aug. 28, 2018

(54) TONER

(71) Applicant: ZEON CORPORATION, Tokyo (JP)

(72) Inventors: Takeshi Hirata, Tokyo (JP); Hiroyuki Taguchi, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 15/552,726

(22) PCT Filed: Feb. 9, 2016

(86) PCT No.: PCT/JP2016/053760
§ 371 (c)(1),
(2) Date: Aug. 22, 2017

(87) PCT Pub. No.: WO2016/136452
PCT Pub. Date: Sep. 1, 2016

(65) Prior Publication Data
US 2018/0067413 A1    Mar. 8, 2018

(30) Foreign Application Priority Data
Feb. 27, 2015    (JP) ................. 2015-038166

(51) Int. Cl.
*G03G 9/08*  (2006.01)
*G03G 9/087*  (2006.01)
*G01N 30/02*  (2006.01)

(52) U.S. Cl.
CPC ......... *G03G 9/08771* (2013.01); *G01N 30/02* (2013.01); *G03G 9/0802* (2013.01); *G03G 9/0815* (2013.01); *G03G 9/08711* (2013.01); *G01N 2030/025* (2013.01)

(58) Field of Classification Search
CPC . G03G 9/08711; G03G 9/0802; G03G 9/0815

USPC ........................................... 430/109.3, 137.1
See application file for complete search history.

(56) References Cited

U.S. PATENT DOCUMENTS

2015/0044604 A1   2/2015  Jin et al.

FOREIGN PATENT DOCUMENTS

| JP | 2000231220 A | 8/2000 |
|----|---|---|
| JP | 2004054256 A | 2/2004 |
| JP | 2007004140 A | 1/2007 |
| WO | 2013/146045 A1 | 10/2013 |

OTHER PUBLICATIONS

Notification of Transmittal of the International Preliminary Report on Patentability (PCT/IB/338) dated Aug. 21, 2017, issued in PCT/JP2016/053760.

*Primary Examiner* — Mark A Chapman
(74) *Attorney, Agent, or Firm* — Westerman, Hattori, Daniels & Adrian, LLP

(57) ABSTRACT

A toner configured to produce less odor in printing and to have excellent charge stability. Disclosed is a toner comprising polymer particles obtained by polymerizing a polymerizable monomer and an external additive attached to a surface of the polymer particles, wherein a volatilization amount a of an alkylthiol with a molecular weight of 110 or more and less than 150 with respect to the toner, which is quantitated at a volatilization temperature of 160° C. in purge & trap/gas chromatography measurement A, is 1 mass ppm or less, and a volatilization amount b of the alkylthiol with respect to the toner, which is quantitated at a volatilization temperature of 220° C. in purge & trap/gas chromatography measurement B, is 30 mass ppm or more and 1,000 mass ppm or less.

2 Claims, 1 Drawing Sheet

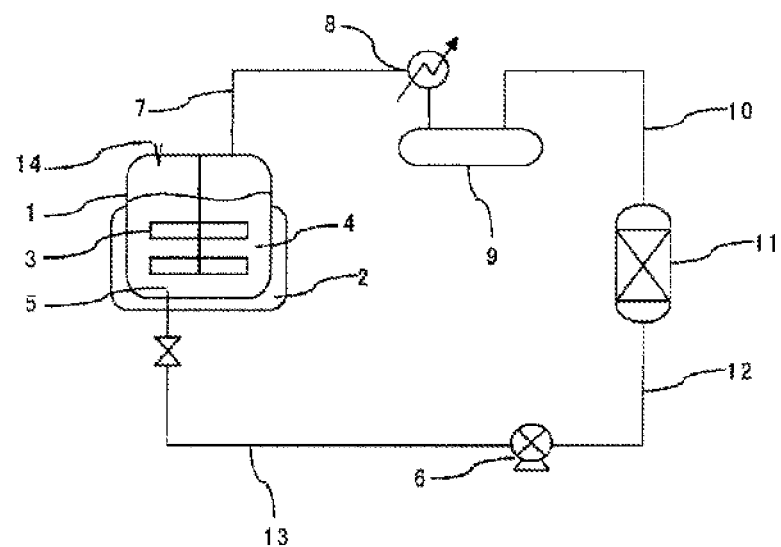

TONER

TECHNICAL FIELD

The present invention relates to a toner configured to be used for development in image forming devices using electrophotography, such as a coping machine, a facsimile machine and a printer.

BACKGROUND ART

Methods for forming a desired image by developing an electrostatic latent image with a toner, have been widely used.

For example, in electrophotography, an electrostatic latent image formed on a photoconductor is developed with a toner made from colored particles optionally containing other particles of an external additive, carrier, etc. Then, the developed image is transferred onto a recording medium such as a paper or OHP sheet and then fixed to obtain a printed product.

There is an increasing need for color image forming devices using electrophotography, such as a color copying machine, a color facsimile machine and a color printer. In the formation of color images by full-color electrophotography, colors are reproduced with color toners in three colors, which are generally yellow, magenta and cyan, or with color toners in a total of four colors, which are the three colors and black. In the case of color copying, an image is formed by the following method, for example: first, a color image is read and decomposed into pixels and then converted to digital image signals in different colors; light is applied onto a charged photoconductor to form an electrostatic latent image; then, the image is developed on the photoconductor, using color toners that correspond to electrostatic latent image signals in different colors; finally, the image is transferred onto a recording medium such as a paper or OHP sheet.

In general, methods for producing toners used for development are broadly classified into a pulverization method and a polymerization method.

In the pulverization method, polymer particles are produced by pulverizing and classifying a solid colored resin product obtained by melt-kneading a binder resin and a colorant.

The polymerization method is a method for producing polymer particles by forming and polymerizing droplets of a polymerizable monomer composition containing a polymerizable monomer and a colorant. While the form of the polymer particles obtained by the pulverization method is not uniform, the form of the polymer particles obtained by the polymerization method is close to a spherical form, and the particles have a small particle diameter and a narrow particle diameter distribution. Especially from the viewpoint of improving image properties such as image reproducibility and fineness, toners with a highly-controlled form and particle diameter distribution, like toners produced by the polymerization method (i.e., polymerized toner), have been increasingly used.

Various kinds of properties are required of toners, such as environmental stability from the viewpoint of preventing image deterioration due to changes in temperature, humidity, etc., printing durability from the viewpoint of reducing toner consumption, and low-temperature fixability from the viewpoint of reducing power consumption.

In the case of toners for developing electrostatic images, toner particles containing polymer particles and an external additive attached thereto are charged and then supplied onto a photoconductor having an electrostatic latent image. Or, the toner particles and a member such as a developing blade are charged in between and then supplied onto a photoconductor having an electrostatic latent image, or the toner particles and a carrier are charged in between and then supplied onto a photoconductor having an electrostatic latent image. In this supplying step, the toner in an amount which corresponds to the charge density of the electrostatic latent image is attached onto the photoconductor. A high-quality image is formed when the toner is appropriately charged.

However, once a decrease or non-uniformity in toner charge amount is caused by environmental changes such as temperature change or humidity change, a desired electrostatic latent image cannot be developed on a photoconductor and results in problems such as fog, unevenness of images, and changes in image density.

To prevent variations in toner charge amount due to environmental changes, various kinds of additives have been studied.

Patent Literature 1 discloses a method for producing a toner for developing electrostatic images, which contains 80 to 500 ppm of a cyano group-containing hydrocarbon compound and a positively-chargeable charge control resin or agent. Also, Patent Literature 1 mentions that the toner is poor in heat-resistant storage stability and printing durability when the cyano group-containing hydrocarbon compound is more than 500 ppm, and the charge stability of the toner deteriorates when the cyano group-containing hydrocarbon compound is less than 80 ppm. However, the toner disclosed in patent Literature 1 has a problem in that a slight amount of the cyano group-containing hydrocarbon compound volatilizes when the toner is fixed.

CITATION LIST

Patent Literature 1: International Publication No. WO2013/146045

SUMMARY OF INVENTION

Technical Problem

An object of the present invention is to produce a toner configured to produce less odor in printing and to have excellent charge stability. Another object of the present invention is to provide a toner configured to have excellent low-temperature fixability in addition to the above.

Solution to Problem

As a result of diligent research, the inventors of the present invention found that the above object can be achieved by incorporating an alkylthiol having specific properties in a toner.

That is, a toner is provided according to the present invention, which is a toner comprising polymer particles obtained by polymerizing a polymerizable monomer and an external additive attached to a surface of the polymer particles, wherein a volatilisation amount a of an alkylthiol with a molecular weight of 110 or more and less than 150 with respect to the toner, which is quantitated at a volatilization temperature of 160° C. in the following purge & trap/gas chromatography measurement A, is 1 mass ppm or less, and a volatilization amount b of the alkylthiol with respect to the toner, which is quantitated at a volatilization temperature of 220° C. in the following purge & trap/gas chromatography measurement B, is 30 mass ppm or more and 1,000 mass ppm or less.

[Purge & Trap/Gas Chromatography Measurement A]

First, 0.1 g of the toner is put in a purge container; with flowing helium gas at 50 mL/min as carrier gas, the purge container is heated from room temperature at a rate of 10° C./min and kept at a temperature of 160° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount a of the alkylthiol with respect to the toner is quantitated by gas chromatography in the following conditions.

[Purge & Trap/Gas Chromatography Measurement B]

First, 0.1 g of the toner is put in a purge container; with flowing helium gas at 50 mL/min as carrier gas, the purge container is heated from room temperature at a rate of 10° C./min and kept at a temperature of 220° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount b of the alkylthiol with respect to the toner is quantitated by gas chromatography in the following conditions.

[Gas Chromatography Conditions]

Column temperature: Increased from 50° C. (kept for 2 minutes) to 270° C. (at 10° C./min)
Sample feeding temperature: 280° C.
Detection temperature: 280° C.
Carrier gas: Helium gas (flow rate: 1 mL/min)

In the present invention, a carbon number of an alkyl group in the alkylthiol is preferably 6 or more and 8 or less.

Advantageous Effects of Invention

The toner of the present invention as described above comprises the alkylthiol with a molecular weight of less than 150, and the volatilization amount of the alkylthiol in a heating condition of 220° C., is 30 mass ppm or more and 1,000 mass ppm or less; therefore, the toner of the present invention is a toner with better charge stability than ever before. On the other hand, for the toner of the present invention as described above, the alkylthiol has a molecular weight of 110 or more, and the volatilization amount of the alkylthiol in a heating condition of 160° C. is 1 mass ppm or less; therefore, the toner of the present invention is a toner that produces less odor than ever before in printing.

BRIEF DESCRIPTION OF DRAWINGS

FIG. 1 is a view showing an example of a system used for stripping treatment.

DESCRIPTION OF EMBODIMENTS

The toner of the present invention comprises polymer particles obtained by polymerizing a polymerizable monomer and an external additive attached to a surface of the polymer particles, wherein a volatilisation amount a of an alkylthiol with a molecular weight of 110 or more and less than 150 with respect to the toner, which is quantitated at a volatilization temperature of 160° C. in the following purge & trap/gas chromatography measurement A, is 1 mass ppm or less, and a volatilization amount b of the alkylthiol with respect to the toner, which is quantitated at a volatilization temperature of 220° C. in the following purge & trap/gas chromatography measurement B, is 30 mass ppm or more and 1,000 mass ppm or less.

[Purge & Trap/Gas Chromatography Measurement A]

First, 0.1 g of the toner is put in a purge container; with flowing helium gas at 50 mL/min as carrier gas, the purge container is heated from room temperature at a rate of 10° C./min and kept at a temperature of 160° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount a of the alkylthiol with respect to the toner is quantitated by gas chromatography in the following conditions.

[Purge & Trap/Gas Chromatography Measurement B]

First, 0.1 g of the toner is put in a purge container; with flowing helium gas at 50 mL/min as carrier gas, the purge container is heated from room temperature at a rate of 10° C./min and kept at a temperature of 220° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount b of the alkylthiol with respect to the toner is quantitated by gas chromatography in the following conditions.

[Gas Chromatography Conditions]

Column temperature: Increased from 50° C. (kept for 2 minutes) to 270° C. (at 10° C./min)
Sample feeding temperature: 280° C.
Detect ion temperature: 280° C.
Carrier gas: Helium gas (flow rate: 1 mL/min)

Hereinafter, the toner of the present invention will be explained. The toner of the present invention contains polymer particles and an external additive.

Hereinafter, a method for producing polymer particles used in the present invention, polymer particles obtained by the production method, a method for producing a toner using the polymer particles, and the toner of the present invention, will be explained in order.

1. The Method for Producing Polymer Particles

The polymer particles of the present invention can be produced by a wet or dry method. Of wet methods, a suspension polymerization method is preferred. The suspension polymerization method is preferably carried out by the following process.

(A) Suspension Polymerization Method
(A-1) Step of Preparing a Polymerizable Monomer Composition First, a polymerizable monomer, a colorant and, as needed, other additive(s) such as a charge control agent, are mixed to prepare a polymerizable monomer composition. In the preparation of the polymerizable monomer composition, the mixing is conducted by a media type dispersing machine, for example.

In the present invention, "polymerizable monomer" means a monomer having a polymerizable functional group, and the polymerizable monomer is polymerized into a binder resin. A mono-vinyl monomer is preferably used as a main component of the polymerizable monomer. Examples of monovinyl monomers include the following: styrene; styrene derivatives such as vinyl toluene and α-methylstyrene; acrylic acids and methacrylic acids; acrylic esters such as methyl acrylate, ethyl acrylate, propyl acrylate, butyl acrylate, 2-ethylhexyl acrylate and dimethylaminoethyl acrylate; methacrylic: esters such as methyl methacrylate, ethyl methacrylate, propyl methacrylate, butyl methacrylate, 2-ethylhexylmethacrylate and dimethylaminoethyl methacrylate; nitrile compounds such as acrylonitrile and methacrylonitrile; amide compounds such as acrylamide and methacrylamide; and olefins such as ethylene, propylene and butylene. These monovinyl monomers can be used alone or in combination of two or more kinds. Of these monovinyl monomers, preferably used are styrene, styrene derivatives, acrylic esters and methacrylic esters.

To prevent hot offset and improve storage stability, it is preferable to use the monovinyl monomer and an optional cross-linkable polymerizable monomer. The cross-linkable polymerizable monomer means a monomer having two or more polymerizable functional groups. Examples of cross-linkable polymerizable monomers include aromatic divinyl compounds such as divinylbenzene, divinylnaphthalene and derivatives thereof; ester compounds such as ethylene glycol dimethacrylate and diethylene glycol dimethacrylate, in which two or more carboxylic acids having a carbon-carbon double bond are esterified to an alcohol having two or more hydroxyl groups; other divinyl compounds such as N,N-divinylaniline and divinyl ether; and compounds having three or more vinyl groups. These cross-linkable polymerizable monomers can be used alone or in combination of two or more kinds.

In the present invention, the cross-linkable polymerizable monomer is used in an amount of generally 0.1 to 5 parts by mass, and preferably 0.3 to 2 parts by mass, relative to 100 parts by mass of the monovinyl monomer.

It is also preferable to use a macromonomer further as a part of the polymerizable monomer, because the toner thus obtained has an excellent balance between storage stability and low-temperature fixability. A macromonomer is one having a polymerizable carbon-carbon unsaturated double bond at an end of a molecular chain thereof, and it is also a reactive oligomer or polymer generally having a number average molecular weight of 1,000 to 30,000. The macromonomer is preferably one that gives a polymer having a higher glass transition temperature (hereinafter may be referred to as "Tg") than that of the polymer obtained by polymerizing the above-mentioned monovinyl monomer. The amount of the macromonomer is used in an amount of preferably 0.03 to 5 parts by mass, and more preferably 0.05 to 1 part by mass, relative to 100 parts by mass of the monovinyl monomer.

A colorant is used in the present invention. In the case of producing a color toner, black, cyan, yellow and magenta colorants can foe used.

As the black colorant, for example, there may be used carbon black, titanium black, and magnetic powders of zinc iron oxide, nickel iron oxide and so on.

As the cyan colorant, for example, there may be used copper phthalocyanine compounds, derivatives thereof, and anthraquinone compounds. Concrete examples include C.I. Pigment Blue 2, 3, 6, 15, 15:1, 15:2, 15:3, 15:4, 16, 17:1 and 60.

As the yellow colorant, for example, there may be used compounds including condensation polycyclic pigments and azo-based pigments such as monoazo pigments, disazo pigments, etc. Examples thereof include C.I. Pigment Yellow 3, 12, 13, 14, 15, 17, 62, 65, 73, 74, 83, 93, 97, 120, 138, 155, 180, 181, 185, 186 and 213.

As the magenta colorant, there may be used compounds including condensation polycyclic pigments and azo-based pigments such as monoazo pigments, disazo pigments, etc. Examples thereof include C.I. Pigment Violet 19 and C.I. Pigment Red 31, 48, 57:1, 58, 60, 63, 64, 68, 81, 83, 87, 88, 89, 90, 112, 114, 122, 123, 144, 146, 149, 150, 163, 170, 184, 185, 187, 202, 206, 207, 209, 237, 233, 251, 254, 255 and 269.

In the present invention, colorants can be used alone or in combination of two or more kinds. The colorant is preferably used in an amount of 1 to 10 parts by mass, relative to 100 parts by mass of the monovinyl monomer.

The toner of the present invention contains the alkylthiol with a molecular weight of 110 or more and less than 150. The alkylthiol may foe contained in the polymer particles, in the below-described external additive, or in both the polymer particles and the external additive. Also, the alkylthiol may exist in the first place as a toner raw material in the production of the toner, or it may be synthesized by a chemical reaction caused in the toner in the toner production. Also, the alkylthiol may be formed in the toner by a time-dependent change after the toner production. That is, as long as the above-specified alkylthiol is contained in the toner, and the volatilization amount of the alkylthiol is within the specific range measured by the below-described purge & trap/gas chromatographies A and B, the toner is included in the present invention.

The specific alkylthiol used in the present invention may be one kind of alkylthiol or two or more kinds of alkylthiols.

A carbon number of an alkyl group in the alkylthiol is preferably 6 or more and 8 or less, more preferably 7 or more and 9 or less, and still more preferably 7. When the carbon number of the alkyl group is less than 6, odor inhibition may be difficult at the time of low-temperature fixing. On the other hand, when the carbon number of the alkyl group is more than 8, the toner thus obtained may have poor charge stability.

The structure of the alkylthiol used in the present invention is not particularly limited, as long as it has at least one of a straight-chain hydrocarbon framework, a branched-chain hydrocarbon framework, and a cyclic hydrocarbon framework, and one hydrogen atom in the hydrocarbon framework is substituted with a mercapto group (—SH).

As the alkylthiol, examples include an alkylthiol having 6 carbon atoms, such as 1-hexanethiol ($CH_3(CH_2)_5SH$, molecular weight: 118.2), 2-hexanethiol ($CH_3(CH_2)_3CH(SH)CH_3$, molecular weight: 118.2) and 3-hexanethiol ($CH_3(CH_2)_2CH(SH)CH_2CH_3$, molecular weight: 118.2); an alkylthiol having 7 carbon atoms, such as 1-heptanethiol ($CH_3(CH_2)_6SH$, molecular weight: 132.3), 2-heptanethiol ($CH_3(CH_2)_4CH(SH)CH_3$, molecular weight: 132.3) and 3-heptanethiol ($CH_3(CH_2)_3CH(SH)CH_2CH_3$, molecular weight: 132.3); and an alkylthiol having 8 carbon atoms, such as 1-octanethiol ($CH_3(CH_2)_7SH$, molecular weight: 146.3), 2-octanethiol ($CH_3(CH_2)_5CH(SH)CH_3$, molecular weight: 146.3) and 3-octanethiol ($CH_3(CH_2)_4CH(SH)CH_2CH_3$, molecular weight: 146.3).

Details of the effect exerted by the addition of the alkylthiol, are not clear; however, the effect is supposed to be due to the following mechanism. In particular, a residue of a peroxide used as a polymerization initiator, etc., is decomposed to produce a polar substance, thereby changing the moisture content of the toner surface especially in a high humidity environment. As a result, a decrease in charge amount generally occurs. However, in the present invention, since the alkylthiol traps the polar substance, it is supposed that excellent charge stability, which is an effect of the present invention, can be exerted.

The alkylthiol may be a previously synthesized one or a commercially-available product. The method for synthesizing the alkylthiol is not particularly limited and may be a conventionally known method.

As the other additive, to increase the charge property of the toner, a positively- or negatively-chargeable charge control agent may be used.

The charge control agent is not particularly limited, as long as it is one that is generally used as a charge control agent for toners. Of charge control agents, a positively- or negatively-chargeable charge control resin is preferred since it has high compatibility with the polymerizable monomer and can impart stable charge property (charge stability) to the particles of the toner. From the viewpoint of obtaining a positively-chargeable toner, a positively-chargeable charge control resin is more preferred.

As the positively-chargeable charge control agent, examples include, but are not limited to, nigrosine dyes; quaternary ammonium salts; triaminotriphenylmethane compounds; imidazole compounds; polyamine resins, quaternary ammonium group-containing copolymers and quaternary ammonium salt group-containing copolymers, which are charge control resins preferably used.

As the negatively-chargeable charge control agent, examples include, but are not limited to, azo dyes containing metals such as Cr, Co, Al and Fe; metal salicylate compounds and metal alkyl salicylate compounds; and charge control resins such as sulfonic acid group-containing copolymers, sulfonic acid salt group-containing copolymers, carboxylic acid group-containing copolymers and carboxylic acid salt group-containing copolymers. Of them, charge control resins are preferred.

In the present invention, the charge control agent is used in an amount of generally 0.01 to 10 parts by mass, and preferably 0.03 to 8 parts by mass, relative to 100 parts by mass of the monovinyl monomer. When the amount of the charge control agent added is less than 0.01 part by mass, fog may be produced. When the amount of the charge control agent added is more than 10 parts by mass, soiling may occur.

From the viewpoint of improving the releasing characteristics of the toner from a fixing roller upon fixing, it is preferable to add a release agent to the polymerizable monomer composition. The release agent is not particularly limited as long as it is one that is generally used as a release agent in toner.

The release agent preferably contains at least one of an ester wax and a hydrocarbon wax. By using these waxes as the release agent, a suitable balance between low-temperature fixability and storage stability can be obtained.

In the present invention, preferably used as the release agent is a polyfunctional ester wax. Examples thereof include: pentaerythritol ester compounds such as pentaerythritol tetrapalmitate, pentaerythritol tetrabehenate and pentaerythritol tetrastearate; glycerin ester compounds such as hexaglycerin tetrabehenate tetrapalmitate, hexaglycerin octabehenate, pentaglycerin heptabehenate, tetraglycerin hexabehenate, triglycerin pentabehenate, diglycerin tetrabehenate, and glycerin tribehenate; and dipentaerythritol ester compounds such as dipentaerythritol hexamyristate and dipentaerythritol hexapalmitate. Of them, preferred are dipentaerythritol ester compounds, and more preferred is dipentaerythritol hexamyristate.

Also in the present invention, preferably used as the release agent is a hydrocarbon wax. Examples thereof include a polyethylene wax, a polypropylene wax, a Fischer-Tropsch wax and a petroleum wax. Of them, preferred are a Fischer-Tropsch wax and a petroleum wax, and more preferred is a petroleum wax.

The hydrocarbon wax has a number average molecular weight of preferably 300 to 800, and more preferably 400 to 600. The hydrocarbon wax has a penetration of preferably 1 to 10, and more preferably 2 to 7, which is measured according to JIS K2235 5.4.

Besides the above release agents, for example, there may be used a natural wax such as jojoba and a mineral wax such as ozokerite.

As the release agent, the above-mentioned waxes can be used alone or in combination of two or more kinds.

The release agent is used in an amount of preferably 0.1 to 30 parts by mass, and more preferably 1 to 20 parts by mass, relative to 100 parts by mass of the monovinyl monomer.

It is also preferable to use a molecular weight modifier as other additive, when polymerizing the polymerizable monomer into a binder resin.

The molecular weight modifier is not particularly limited, as long as it is one that is generally used as a molecular weight modifier for toner. Examples thereof include mercaptans such as t-dodecyl mercaptan, n-dodecyl mercaptan, n-octyl mercaptan and 2,2,4,6,6-pentamethylheptane-4-thiol; and thiuram disulfides such as tetramethylthiuram disulfide, tetraethylthiuram disulfide, tetrabutylthiuram disulfide, N,N'-dimethyl-N,N'-diphenylthiuram disulfide, and N,N'-dioctadecyl-N,N'-diisopropylthiuram disulfide. These molecular weight modifiers can be used alone or in combination of two or more kinds.

In the present invention, the molecular weight modifier is used in an amount of generally 0.01 to 10 parts by mass, and preferably 0.1 to 5 parts by mass, relative to 100 parts by mass of the monovinyl monomer.

(A-2) Suspension Step for Obtaining a Suspension (Droplets Forming Step)

In the present invention, the polymerizable monomer composition containing at least the polymerizable monomer is dispersed in an aqueous medium containing a dispersion stabilizer. After adding a polymerization initiator thereto, the polymerizable monomer composition is formed into droplets. The method for forming droplets is not particularly limited. For example, a machine which is capable of strong agitation is used, such as an (in-line) emulsification device (product name: MILDER, manufactured by: Pacific Machinery & Engineering Co., Ltd.), a high-speed emulsification device (product name: T.K. HOMO MIXER MARK II, manufactured by: RRIMIX Corporation), etc.

As the polymerization initiator, for example, there may be mentioned persulfates such as potassium persulfate and ammonium persulfate; azo compounds such as 4,4-azobois (4-cyanovaleric acid), 2,2'-azobis(2-methyl-N-(2-hydroxyethyl)propion amide), 2,2'-azobis(2-amidinopropane)dihydrochloride, 2,2'azobis(2,4-dimethylvaleronitrile) and 2,2'-azobisisobutyronitrile; and organic peroxides such as di-t-butyl peroxide, benzoyl peroxide, t-butylperoxy-2-ethylhexanoate, t-butylperoxy-2-ethylbutanoate, t-hexylperoxy-2-ethylbutanoate, diisopropyl peroxydicarbonate, di-t-butylperoxy isophthalate and t-butylperoxy isobutyrate. They may be used alone or in combination of two or more kinds. Of them, preferably used are organic peroxides, because they can decrease polymerizable monomer residues and they have excellent printing durability.

Of organic peroxides, preferred are those containing no cyano group, more preferred are peroxyesters, and still more preferred are non-aromatic peroxyesters, i.e., peroxyesters containing no aromatic ring, because they have excellent polymerization initiation efficiency and can decrease polymerizable monomer residues.

As described above, the polymerization initiator can be added after dispersing the polymerizable monomer composition in the aqueous medium and before forming droplets. Or, it can be added to the polymerizable monomer composition before dispersing the composition in the aqueous medium.

The added amount of the polymerization initiator, which is used for polymerization of the polymerizable monomer composition, is preferably 0.1 to 20 parts by mass, more preferably 0.3 to 15 parts by mass, and still more preferably 1 to 10 parts by mass, relative to 100 parts by mass of the monovinyl monomer.

In the present invention, "aqueous medium" means a medium which mainly consists of water.

In the present invention, the aqueous medium preferably contains a dispersion stabilizer. As the dispersion stabilizer, for example, there may be mentioned the following compounds: inorganic compounds including sulfates such as barium sulfate and calcium sulfate; carbonates such as barium carbonate, calcium carbonate and magnesium carbonate; phosphates such as calcium phosphate; metal oxides such as aluminum oxide and titanium oxide; and metal hydroxides such as aluminum hydroxide, magnesium hydroxide and iron(II)hydroxide; and organic compounds including water-soluble polymers such as polyvinyl alcohol, methyl cellulose and gelatin; anionic surfactants; nonionic surfactants; and ampholytic surfactants. These dispersion stabilizers can be used alone or in combination of two or more kinds.

Of the above dispersion stabilisers, preferred are inorganic compounds, and particularly preferred are colloids of hardly water-soluble metal hydroxides. By using such colloids, the particle diameter distribution of the polymer particles can be adjusted to be narrow and, after washing, the amount of dispersion stabilizer residues can be decreased. Therefore, the toner thus obtained can sharply reproduce an image and has excellent environmental stability.

(A-3) Polymerization Step

Droplets are formed as described above under (A-2), and the thus-obtained aqueous dispersion medium is heated to initiate polymerization, thus producing an aqueous dispersion of the polymer particles.

The polymerization temperature of the polymerizable monomer composition is preferably 50° C. or more, and more preferably 60 to 95° C. The polymerization reaction time is preferably 1 to 20 hours, and more preferably 2 to 15 hours.

The polymer particles can be mixed with an external additive and then used as a toner. However, it is preferable to produce core-shell type (or capsule type) polymer particles, by using the polymer particles as the core layer and forming a shell layer outside the core layer. By covering the core layer, which is made of a substance having a low softening point, with a substance having a higher softening point, the core-shell type polymer particles can achieve a balance between lowering the fixation temperature and preventing aggregation during storage.

The method for producing the core-shell type polymer particles using the above-mentioned polymer particles, is not particularly limited. The core-shell type polymer particles can be produced by conventionally-known methods. From the viewpoint of production efficiency, preferred are an in-situ polymerization method and a phase separation method.

Hereinafter, the method for producing the core-shell type polymer particles by the in-situ polymerization method, will be explained.

First, a polymerizable monomer for forming the shell layer (polymerizable monomer for shell) and a polymerization initiator are added to an aqueous medium for polymerization, in which the polymer particles are dispersed, thereby obtaining the core-shell type polymer particles.

As the polymerizable monomer for shell, the above-mentioned polymerizable monomers can be used. Of them, it is preferable to use monomers which can provide a polymer having a Tg of more than 80° C., such as styrene, acrylonitrile and methyl methacrylate, alone or in combination of two or more kinds.

As the polymerization initiator that is used for polymerization of the polymerizable monomer for shell, for example, there may be mentioned water-soluble polymerization initiators including metal persulfates such as potassium persulfate and ammonium persulfate; and azo-based initiators such as 2,2'-azobis(2-methyl-N-(2-hydroxyethyl) propionamide) and 2,2'-azobis(2-methyl-N-(1,1-bis(hydroxymethyl)2-hydroxyethyl)propionamide). They can be used alone or in combination of two or more kinds. The polymerization initiator is used in an amount of preferably 0.1 to 30 parts by mass, and more preferably 1 to 20 parts by mass, relative to 100 parts by mass of the polymerizable monomer for shell.

The polymerization temperature of the shell layer is preferably 50° C. or more, and more preferably 60 to 95° C. The polymerization reaction time is preferably 1 to 20 hours, and more preferably 2 to 15 hours.

(A-4) Washing, Filtering, Dehydrating and Drying Steps

After the polymerization is completed, preferably, the aqueous dispersion of the polymer particles obtained by the polymerization is subjected to repeated cycles of filtering, washing (for removal of the dispersion stabilizer), dehydrating and drying, as needed, according to a known method.

Before subjected to the cycles of washing, filtering, dehydrating and drying, the aqueous dispersion of the polymer particles can be subjected to a stripping step, for the purpose of removing volatile substances (mainly such as ether components and styrene) from the polymer particles.

An example of the stripping step is explained now. Stripping treatment can be carried out as follows on the thus-obtained aqueous dispersion of the polymer particles by an air injection method, using the stripping treatment system shown in FIG. 1.

First, an aqueous dispersion of polymer particles (hereinafter referred to as aqueous dispersion 4) is diluted with ion-exchanged water to a predetermined solid concentration and then supplied to an evaporator 1. As needed, a predetermined amount of defoaming agent is put in the evaporator 1. Inert gas (e.g., nitrogen gas) or saturated water vapor is injected into the evaporator 1 to replace the gas phase part inside the evaporator therewith.

Next, the evaporator 1 is heated by supplying hot water to a jacket 2, which is provided outside and in contact with the evaporator 1, while agitating the aqueous dispersion 4 with an agitator 3 at a predetermined rotational frequency, the agitator being furnished with agitating blades. After the liquid temperature of the aqueous dispersion 4 is increased to a predetermined temperature, a blower 6 is started to adjust the flow rate of the inert gas. Then, volatile substances are removed from the polymer particles (stripping treatment) by injecting the inert gas into the aqueous dispersion 4 through a gas intake tube 5, the tube having a gas intake part in a straight tube form. The stripping treatment can be carried out while keeping the foam level of the aqueous dispersion 4 at 90 to 35%.

After the stripping treatment is carried out for a predetermined period of time, the aqueous dispersion 4 is cooled by supplying cooling water to the jacket 2, which is provided outside and in contact with the evaporator until the liquid temperature reaches 25° C. The stripping is completed when the temperature reaches 25° C.

Washing is preferably carried out by the following method: in the case of using an inorganic compound as the dispersion stabilizer, by adding an acid or alkali to the aqueous dispersion, the dispersion stabilizer is dissolved in water and then removed. In the case of using a colloid of a hardly water-soluble inorganic hydroxide as the dispersion stabilizer, it is preferable to add an acid to adjust the pH of the aqueous dispersion to pH 6.5 or less. As the acid added, there may foe used inorganic acids such as sulfuric acid, hydrochloric acid and nitric acid, and organic acids such as formic acid and acetic acid. Sulfuric acid is particularly preferred, because of large removal efficiency and small pressure on production facilities.

Dehydrating and filtering can be carried out by various kinds of known methods, and the methods are not particularly limited. For example, there may be mentioned a centrifugal filtration method, a vacuum filtration method, a pressure filtration method, etc. Drying can be also carried out by various kinds of methods, and the methods are not particularly limited.

(B) Pulverization Method

In the case of producing the polymer particles by the pulverization method, it is carried out by the following process.

First, a binder resin, a colorant and, as needed, other additive(s) such as a charge control agent, are mixed by a mixer such as a ball mill, V-mixer, FM MIXER (product name), high-speed dissolver, internal mixer, a whole burg, etc. Next, the thus-obtained mixture is kneaded by a pressure kneader, biaxial kneading extruder, roller or the like, while heating the mixture. The thus-obtained kneaded product is coarsely pulverized by a pulverizer such as a hammer mill, cutter mill, roller mill, etc. In addition, the resultant is finely pulverized by a pulverizer such as a jet mill, high-speed rotating pulverizer or the like and then classified into a desired particle diameter by a classifier such as a pneumatic classifier or airflow classifier, thus obtaining polymer particles produced by the pulverization method.

As the raw materials used in the pulverization method, that is, as the binder resin, the colorant and, as needed, other additive(s) such as a charge control agent, those mentioned above under "(A) Suspension polymerization method" can be used. As well as the polymer particles obtained by the method mentioned above under "(A) Suspension polymerization method", the polymer particles produced by the pulverization method can be also formed into core-shell type polymer particles by the in-situ polymerization method, etc.

As the binder resin, there may be also used resins that have been widely used in toner. Concrete examples of the binder resin used in the pulverization method include polystyrene, styrene-butyl acrylate copolymer, polyester resin and epoxy resin.

2. Polymer Particles

The polymer particles are obtained by production methods such as those mentioned under "(A) Suspension polymerization method" and "(B) Pulverization method".

Hereinafter, the polymer particles that constitute the toner will be explained. The polymer particles explained below encompass both core-shell type polymer particles and other types of polymer particles.

The polymer particles have a volume average particle diameter (Dv) of preferably 4 to 12 µm, and more preferably 5 to 10 µm. When the Dv is less than 4 µm, toner flowability is decreased and may result in poor transferability or decrease in image density. When the Dv is more than 12 µm, image resolution may foe decreased.

As for the polymer particles, the ratio (Dv/Dn) of the volume average particle diameter (Dv) to the number average particle diameter (Dn) is preferably 1.0 to 1.3, more preferably 1.0 to 1.2.

When the Dv/Dn is more than 1.3, there may be a decrease in transferability, image density and resolution. The volume and number average particle diameters of the polymer particles can be measured by a particle size analyzer (product name: Multisizer, manufactured by: Beckman Coulter, Inc.), for example.

From the viewpoint of image reproducibility, the polymer particles of the present invention preferably have an average circularity of 0.96 to 1.00, more preferably 0.97 to 1.00, still more preferably 0.98 to 1.00.

When the polymer particles have an average circularity of less than 0.96, thin line reproducibility may be deteriorated.

In the present invention, "circularity" is defined as a value which is obtained by dividing the circumference of a circle having the same projected area as that of a projected image of a particle by the circumference of the projected image of the particle. Also in the present invention, "average circularity" is used as a simple method for quantitatively describing the form of the particles and is an indicator that shows the degree of the surface roughness of the polymer particles. The average circularity is 1 when the polymer particles are perfectly spherical, and it gets smaller as the surface shape of the polymer particles becomes more complex.

The polymer particles of the present invention have a sphericity (Sc/Sr) of preferably 1.0 to 1.3, and more preferably 1.0 to 1.2. In the case of using the polymer particles having a sphericity of more than 1.3, the transferability or flowability of the toner decreases, and blurring may easily occur.

The sphericity of each polymer particle is a value obtained by dividing the area (Sc) of a circle having the maximum absolute length of the particle as its longer diameter by the substantial projected area (Sr) of the particle. Specifically, an electron micrograph of the polymer particles is taken, and the micrograph is measured by image analyzer LUZEX IID (product name, manufactured by Nireco Corporation) in the condition that the area ratio of particles with respect to the frame area is up to 2%, and the total number of processed particles is 100. In the present invention, the sphericity is the average of the 100 processed particles.

3. Toner Production Method

In the present invention, an external additive is attached to the surface of the polymer particles by mixing the polymer particles with the external additive and agitating them, thus obtaining a one-component toner (developer).

The one-component toner can be further mixed with carrier particles and agitated to obtain a two-component developer.

The agitator used for the attachment is not particularly limited, as long as it is an agitator that is able to attach the external additive to the surface of the polymer particles. The attachment can be carried out by an agitator that is capable of mixing and agitating, such as FM Mixer (product name, manufactured by: Nippon Coke & Engineering Co., Ltd.), Super Mixer (product name, manufactured by: Kawata Mfg. Co., Ltd.), Q Mixer (product name, manufactured by: Nippon Coke & Engineering Co., Ltd.), Mechanofusion system (product name, manufactured by: Hosokawa Micron Corporation) or Mechanomill (product name, manufactured by: Okada Seiko Co., Ltd.)

As the external additive, there may be mentioned inorganic fine particles of silica, titanium oxide, aluminum oxide, sine oxide, tin oxide, calcium carbonate, calcium phosphate, cerium oxide and so on, and organic particles of polymethyl methacrylate resin, silicone resin, melamine resin and so on. Of them, preferred are inorganic fine particles. Of inorganic fine particles, preferred are inorganic fine particles of silica and titanium oxide, and particularly preferred are inorganic fine particles of silica.

These external additives can foe used alone or in combination of two or more kinds. It is particularly preferable to use two more kinds of silica particles having different particle diameters.

In the present invention, the external additive is used in an amount of generally 0.05 to 6 parts by mass, and preferably 0.2 to 5 parts by mass, relative to 100 parts by mass of the polymer particles. When the amount of the external additive added is less than 0.05 part by mass, toner transferability may lower. When the amount of the external additive added is more than 6 parts by mass, fog may be produced.

4. Toner of the Present Invention

The toner of the present invention produces less odor in printing, has excellent charge stability, and also has excellent low-temperature fixability.

The toner of the present invention is needed to satisfy the following conditions (α) and (β) in the purge & trap/gas chromatography measurements A and B in specific conditions, respectively.

(α) The volatilization amount a of the alkylthiol with respect to the toner, which is quantitated at a volatilization temperature of 160° C., is 1 mass ppm or less.

(β) The volatilization amount b of the alkylthiol with respect to the toner, which is quantitated at a volatilization temperature of 220° C., is 30 mass ppm or more and 1,000 mass ppm or less.

By satisfying the condition (β), a toner with better charge stability than ever before is provided.

Meanwhile, by satisfying the condition (α), a toner that produces less odor than ever before in printing, is provided.

In the present invention, the purge & trap/gas chromatography measurement A is as follows.

First, 0.1 g of the toner is put in a purge container; with flowing helium gas at 50 mL/min as carrier gas, the purge container is heated from room temperature at a rate of 10° C./min and kept at a temperature of 160° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount a of the alkylthiol with respect to the toner is quantitated by gas chromatography in specific conditions.

In the present invention, the gas chromatography conditions are as follows.

Column temperature: Increased from 50° C. (kept for 2 minutes) to 270° C. (at 10° C./min)
Sample feeding temperature: 280° C.
Detection temperature: 280° C.
Carrier gas: Helium gas (flow rate: 1 mL/min)

In the present invention, the purge & trap/gas chromatography measurement B is as follows.

First, 0.1 g of the toner is put in a purge container; with flowing helium gas at 50 mL/min as carrier gas, the purge container is heated from room temperature at a rate of 10° C./min and kept at a temperature of 220° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount b of the alkylthiol with respect to the toner is quantitated by gas chromatography in the above conditions.

As just described, the measurement B is the same as the measurement A, except that the initially kept temperature is changed from 160° C. to 220° C.

Qualitative analysis of the volatile component can be carried out by a gas chromatography mass spectrometer (GC/MS), etc.

EXAMPLES

Hereinafter, the present invention will be explained in more detail, by way of examples and comparative examples. However, the present invention is not limited to the examples. All designations of part(s) and % are expressed on mass basis, unless otherwise noted.

1. Production of Toner for Developing Electrostatic Images

Example 1

The following raw materials were mixed and agitated by an agitator. Then, the mixture was uniformly dispersed by a media type dispersing machine.

Monovinyl monomer: 75 Parts of styrene and 25 parts of n-butyl acrylate (The thus-obtained copolymer has a Tg of 44° C.)

Cyan colorant: 6 Parts of copper phthalocyanine pigment (C.I. Pigment Blue 15:3)

Positively-chargeable charge control agent: 0.5 Part of a positively-chargeable charge control resin (a quaternary ammonium salt group-containing copolymer (product name: FCA-161P, manufactured by: Fujikura Kasei Co., Ltd., a styrene acrylic resin containing 8% by mass of a quaternary ammonium salt group-containing (meth)acrylate monomer unit, Tg: 60° C., Mw: 21,000))

0.25 Part of a polymethacrylic acid ester macro-monomer (product name: AA6, manufactured by: TOAGOSEI Co., Ltd., Tg: 94° C.)

The following raw materials were added to the mixture, mixed and dissolved, thus obtaining a polymerizable monomer composition.

Release agent: 5 Parts of dipentaerythritol hexamyristate (solubility in styrene: 10 g or more/100 g, endothermic peak: 65° C., molecular weight: 1,514)

Alkylthiol: 0.25 Part of 3-heptanethiol (molecular weight: 132.3)

An aqueous solution of 4.9 parts of sodium hydroxide (alkali metal hydroxide) dissolved in 50 parts of ion-exchange water, was gradually added, with agitation, to an aqueous solution of 8.8 parts of magnesium chloride (water-soluble polyvalent metal salt) dissolved in 250 parts of ion-exchange water, thus preparing a magnesium hydroxide colloid dispersion (hardly water-soluble metal hydroxide colloid dispersion).

The particle diameter distribution of the magnesium hydroxide colloid obtained was measured with a particle diameter distribution analyzer (product name: SALD, manufactured by: Shimadzu Corporation). As a result, the particle diameter was found to be as follows: D50 (50% of the cumulative value of number particle diameter distribution) was 0.42 μm, and D90 (90% of the cumulative value of number particle diameter distribution) was 0.82 μm.

To the magnesium hydroxide colloid dispersion obtained above, the polymerizable monomer composition was added at room temperature and agitated until the droplets became stable. To the resultant, the following raw materials were added:

- Polymerization initiator: 5 Parts of t-butylperoxy-2-ethylbutanoate (product name: Trigonox 27, manufactured by: Akzo Nobel, purity: 98%, molecular weight: 188, one-hour half-life temperature: 94° C.)
- Molecular weight modifier: 1.2 Parts of t-dodecyl mercaptan
- Cross-linkable polymerizable monomer: 0.5 Part of divinylbenzene Then, the mixture was subjected to high shear agitation with an in-line emulsification device (product name: MILDER, manufactured by: Pacific Machinery & Engineering Co., Ltd.) at a rotational frequency of 15,000 rpm for 10 minutes, thus forming droplets of the polymerizable monomer composition.

The thus-obtained suspension in which the droplets of the polymerizable monomer composition were dispersed (polymerizable monomer composition dispersion) was put in a reactor furnished with agitating blades. The reactor temperature was increased to 90° C. to initiate polymerization reaction. When the polymerization conversion rate reached 95%, the following raw materials were added thereto.

- Polymerizable monomer for shell: 1 Part of methyl methacrylate
- Polymerization initiator for shell: 0.1 Part of 2,2'-azobis(2-methyl-N-(2-hydroxyethyl)-propionamide) (product name: VA-086, manufactured by: Wako Pure Chemical Industries, Ltd.) dissolved in 10 parts of ion-exchange water The reaction was kept at 90° C. for 3 hours and stopped, thus obtaining an aqueous dispersion of polymer particles having a core-shell structure and a pH of 9.5.

Stripping treatment was carried out as follows on the aqueous dispersion of the polymer particles obtained as described above, by the air injection method and in the stripping treatment system shown in FIG. 1.

First, the aqueous dispersion of the polymer particles (hereinafter referred to as aqueous dispersion 4) was diluted with ion-exchange water to a solid concentration of 20% and then supplied to an evaporator 1. Then, 0.1 part of a de foaming agent (product name: SN Defoamer 180, manufactured by: San Nopco Limited) was put in the evaporator 1. Nitrogen gas was injected into the evaporator 1 to replace the gas phase part inside the evaporator with the nitrogen gas.

Nest, while being agitated with an agitator 3, the aqueous dispersion 4 was heated to 80° C., the agitator being furnished with agitating blades. Then, a blower 6 was started; the flow rate of the nitrogen gas was adjusted to 0.6 m$^3$/(hr·kg); the nitrogen gas was injected into the aqueous dispersion 4 through a gas intake tube 5, the tube having a gas intake part in a straight tube form; and volatile substances were removed from the polymer particles, therefore.

After the stripping treatment, the nitrogen gas passed through a gas circulation line 7 and was introduced to a condenser 8 and then to a condensation tank 9 for condensation. The condensed nitrogen gas passed through a gas circulation line 10 and was introduced to a volatile substance removal device (an adsorption tower filled with activated carbon) 11 to remove volatile substances from the nitrogen gas. The volatile substance-free nitrogen gas passed through a gas circulation line 12 and was injected into the evaporator 1 again, through the blower 6 and then through a gas circulation line 13.

The stripping treatment was carried out in the following condition.

Temperature of the aqueous dispersion 4: 80° C.
Pressure inside the evaporator 1: 101 kPa
Flow rate of the nitrogen gas: 0.6 m$^3$/(hr·kg)
Treatment time: 6 Hours After the six hours of treatment, the aqueous dispersion 4 was cooled to room temperature.

Thereafter, acid washing was carried out on the aqueous dispersion 4, in which sulfuric acid was added to the aqueous dispersion to adjust the pH of the aqueous dispersion to 6.5 or less, while agitating the aqueous dispersion at room temperature. Then, water washing was carried out thereon, in which water was separated from the aqueous dispersion 4 by filtration, followed by addition of another 500 parts of ion-exchange water to turn the dispersion into a slurry again. Thereafter, dehydration and the water washing were further carried out on the thus-obtained slurry repeatedly several times. After the polymer particles were separated by filtration, the separated particles were put in a dryer and dried at 30° C. for one day.

The thus-obtained polymer particles had a volume average particle diameter (Dv) of 9.3 μm and a particle diameter distribution (Dv/Dn) of 1.14. The thickness of the shell was calculated from the volume of the polymerizable monomer for shell and the particle diameter of the core particles (polymer particles before subjected to shell formation) and found to be 0.03 μm. Also, the polymer particles had a sphericity (Sc/Sr) of 1.2.

To 100 parts of the polymer particles obtained above, 0.6 part of hydrophobized fine silica particles (product name: TG820F, manufactured by: Cabot Corporation) and 1.0 part of hydrophobized fine silica particles (product name: NA50Y, manufactured by: Nippon Aerosil Co., Ltd.) were added and mixed with a high-speed agitator (Product name: FM MIXER, manufactured by: Nippon Coke & Engineering Co., Ltd.), thus producing a toner for developing electrostatic images of Example 1, which is a non-magnetic one-component toner. The toner was used in the tests mentioned below.

Example 2

A toner for developing electrostatic images of Example 2 was produced in the same manner as Example 1, except that the amount of the 3-heptanethiol added was changed from 0.25 part to 0.55 part. The toner was used in the tests mentioned below.

Example 3

A toner for developing electrostatic images of Example 3 was produced in the same manner as Example 1, except that 0.25 part of the 3-heptanethiol was changed to 0.30 part of 2-hexanethiol. The toner was used in the tests mentioned below.

Example 4

A toner for developing electrostatic images of Example 4 was produced in the same manner as Example 1, except that 0.25 part of the 3-heptanethiol was changed to 0.60 part of 2-hexanethiol. The toner was used in the tests mentioned below.

Example 5

A toner for developing electrostatic: images of Example 5 was produced in the same manner as Example 1, except that 0.25 part of the 3-heptanethiol was changed to 0.28 part of 1-octanethiol. The toner was used in the tests mentioned below.

Comparative Example 1

A toner for developing electrostatic images of Comparative Example 1 was produced in the same manner as Example 1, except that the 3-heptanethiol was not added. The toner was used in the tests mentioned below.

Comparative Example 2

A toner for developing electrostatic images of Comparative Example 2 was produced in the same manner as Example 1, except that 0.25 part of the 3-heptanethiol was changed to 2.0 parts of 3-pentanethiol. The toner was used in the tests mentioned below.

Comparative Example 3

A toner for developing electrostatic images of Comparative Example 3 was produced in the same manner as Example 1, except that 0.25 part of the 3-heptanethiol was changed to 0.30 part of 3-pentanethiol. The toner was used in the tests mentioned below.

Comparative Example 4

A toner for developing electrostatic images of Comparative Example 4 was produced in the same manner as Example 1, except that 0.25 part of the 3-heptanethiol was changed to 0.10 part of 2-decanethiol. The toner was used in the tests mentioned below.

Comparative Example 5

A toner for developing electrostatic images of Comparative Example 5 was produced in the same manner as Example 1, except that 0.25 part of the 3-heptanethiol was changed to 0.20 part of 2-decanethiol. The toner was used in the tests mentioned below.

2. Evaluation of Toners for Developing Electrostatic Images

The toners of Examples 1 to 5 and Comparative Examples 1 to 5 were evaluated for their properties. Details are as follows.

2-1. Purge & Trap/Gas Chromatography Measurements
(a) Measurement A

First, 0.1 g of the toner was put in a purge container; with flowing helium gas at 50 mL/min as carrier gas, the purge container was heated from room temperature at a rate of 10° C./min and kept at a temperature of 160° C. for 30 minutes; a volatile component thus produced was trapped in a trap tube at −130° C.; and next, with heating the trap tube from −130° C. to 280° C. at a rate of 50° C./min, in which the volatile component was trapped, the volatilization amount a of the alkylthiol with respect to the toner was quantitated by gas chromatography in the following conditions. In the following Table 1, the results of the measurement A are shown as "Volatilization amount a (mass ppm) at 160° C.".

[Gas Chromatography Conditions]
    Column temperature: Increased from 50° C. (kept for 2 minutes) to 270° C. (at 10° C./min)
    Sample feeding temperature: 280° C.
    Detection temperature: 280° C.
    Carrier gas: Helium gas (flow rate: 1 mL/min)

(b) Measurement B

First, 0.1 g of the toner was put in a purge container; with flowing helium gas at 50 mL/min as carrier gas, the purge container was heated from room temperature at a rate of 10° C./min and kept at a temperature of 220° C. for 30 minutes; a volatile component thus produced was trapped in a trap tube at −130° C.; and next, with heating the trap tube from −130° C. to 280° C. at a rate of 50° C./min, in which the volatile component was trapped, the volatilization amount b of the alkylthiol with respect to the toner was quantitated by gas chromatography in the above conditions. The measurement B is the same as the measurement A, except that the initially kept temperature was changed from 160° C. to 220° C. In the following Table 1, the results of the measurement B are shown as "Volatilization amount b (mass ppm) at 220° C.".

2-2. Printing Test

A commercially-available, non-magnetic one-component development printer was used. Printing sheets were loaded in the printer. The toner was put in the toner cartridge of the printer. The toner cartridge was put in a polyvinyl chloride bag. The bag was hermetically closed and stored in an environment at a temperature of 30° C. and a humidity of 50%, for a long period of time for 60 days. Then, fog values were measured as follows in a high temperature and high humidity (H/H) environment at a temperature of 30° C. and a humidity of 80%.

Solid pattern printing (image density 0%) was carried out. When printing halfway, the printer was stopped. An adhesive tape (product name: Scotch Mending Tape 810-3-18, manufactured by: Sumitomo 3M Limited) was attached to the toner in a non-image area on the photoconductor after development. Then, the tape was removed therefrom and attached to a printing sheet. Next, the printing sheet on which the adhesive tape was attached, was measured for color tone with a spectrocolorimeter (product name: SE-2000, manufactured by: Nippon Denshoku Industries Co., Ltd.) In the same manner, as a reference, an unused adhesive tape was attached to the printing sheet and measured it for color tone. A color difference calculated from the color tones was used as the fog value. As the fog value gets smaller, fog decreases and produces an excellent result.

After the above-mentioned long period of storage, continuous printing was carried out at an image density of 1%, in a high temperature and high humidity (H/H) environment at a temperature of 30° C. and a humidity of 80%. The fog value was measured for every 500 sheets. The number of sheets showing a fog value of 1 or more (the number of sheets printed until the appearance of fog) was counted. The printing durability test was carried out on 16,000 printing sheets and stopped on the way when the fog value reached 1.

2-3. Minimum Fixing Temperature

A toner fixing test was carried out as follows with the use of a commercially available, non-magnetic one-component development printer (printing rate: 32 sheets/min) modified to be able to change the temperature of its fixing roller. The toner cartridge in the development device of the printer was filled with 100 g of a toner. Then, printing sheets were loaded in the printer.

In the toner fixing test, solid pattern printing (image density 100%) was carried out. The temperature of the fixing roller in the modified printer was changed by 5° C. from 200° C. to a low temperature range, and a toner-fixing rate was measured at each changed temperature to determine the relationship between the temperature and the toner fixing rate. For every 5° C. decrease in temperature, the fixing roller was kept at that temperature for 5 minutes or more to stabilize the temperature of the fixing roller.

Peeling off of a piece of tape was carried out on an area where the solid pattern (image density 100%) was printed. The toner fixing rate was calculated from the ratio of image densities before and after the peeling off of the piece of tape.

shown in Table 1, along with the type and so on of the alkylthiols. In Table 1, "<0.1" means that the volatilization amount of the alkylthiol is smaller than 0.1 mass ppm, which is a detection limit, and ">16000" means that the fog value is less than 1 even when 16,000 sheets are continuously printed.

TABLE 1

| | | | Alkylthiol | | | | | |
|---|---|---|---|---|---|---|---|---|
| | Compound | Molecular weight | Volatilization amount a (mass ppm) at 160° C. | Volatilization amount b (mass ppm) at 220° C. | HH initial | Durability (sheets) | Minimum fixing temperature (° C.) | Odor sensory test |
| Example 1 | 3-Heptanethiol | 132.3 | 0.38 | 48 | 0.8 | >16000 | 160 | 1 |
| Example 2 | 3-Heptanethiol | 132.3 | 0.84 | 163 | 1.0 | 14500 | 155 | 2 |
| Example 3 | 2-Hexanethiol | 118.2 | 0.40 | 58 | 0.9 | 15000 | 160 | 1 |
| Example 4 | 2-Hexanethiol | 118.2 | 0.74 | 220 | 1.1 | 14000 | 155 | 2 |
| Example 5 | 1-Octanethiol | 146.3 | 0.29 | 32 | 0.9 | 15500 | 160 | 1 |
| Comparative Example 1 | — | — | <0.1 | <0.1 | 1.8 | 12500 | 170 | 1 |
| Comparative Example 2 | 3-Pentanethiol | 104.2 | 3.8 | 1850 | 1.0 | >15000 | 155 | 3 |
| Comparative Example 3 | 3-Pentanethiol | 104.2 | 0.51 | 63 | 0.9 | >15000 | 160 | 3 |
| Comparative Example 4 | 2-Decanethiol | 174.4 | 0.31 | 18 | 1.7 | 12000 | 170 | 1 |
| Comparative Example 5 | 2-Decanethiol | 174.4 | 0.48 | 60 | 1.6 | 13000 | 160 | 1 |

Specifically, the toner fixing rate can be calculated by the following calculation formula 2:

Toner Fixing Rate (%)= ($ID$(after)/$ID$(before))×100  Calculation Formula 2 where "ID (before)" is the image density before the peeling off of the piece of tape, and "ID (after)" is the image density after the peeling off of the piece of tape.

The peeling off operation of the piece of tape consists of the following set of operations: a piece of adhesive tape (product name: Scotch Mending Tape 810-3-18, manufactured by: Sumitomo 3M Limited) is put on a measurement area on a test paper sheet, attached thereto by pressing at a constant pressure with a metal roller disk (diameter 15 cm, thickness 2 cm, weight 1 kg) and then peeled off in a direction along the paper at a constant speed. The image densities were measured by a reflection image densitometer (product name: RD914, manufactured by: Macbeth Process Measurements Co.)

In this toner fixing test, the minimum fixing roller temperature at which the toner fixing rate reached 80% or more, was determined as the minimum fixing temperature of the toner.

2-4. Odor Sensory Test

Solid pattern printing (image density 100%) was carried out. Odor emitted from the fan of the printer was sniffed to measure the intensity of the odor. The odor intensity measurement was carried out by eight panelists on a 0-6 scale. For each sample, the most common score was determined as the evaluation result of the sample. The scores of the odor sensory test represent the following:

0: No odor
1: Odor that can be slightly detected
2: Weak odor that allows to identify what the odor is
3: Odor that can be easily detected
4: Strong odor
5: Intense odor The measurement and evaluation results of the toners of Examples 1 to 5 and Comparative Examples 1 to 5 are 3. Evaluation of Toners Hereinafter, the evaluation results of the toners for developing electrostatic images will be discussed with reference to Table 1.

According to Table 1, the toner of Comparative Example 1 is such a toner that the volatilization amounts of the alkylthiol at 160° C. and 220° C. are both smaller than 0.1 mass ppm. The score of the odor sensory test is as low as 1. However, the initial fog value in the high temperature and high humidity (H/H) environment after the long period of storage, is as high as 1.8, and the number of sheets for the evaluation of durability remained at 12,500 sheets. Therefore, it is clear that the toner of Comparative Example 1 has poor charge stability, and the minimum fixing temperature of the toner is as high as 170° C.

According to Table 1, the toner of Comparative Example 2 is such a toner that the volatilization amount a of the alkylthiol with a molecular weight of 104.2 at 160° C., is 3.8 mass ppm, and the volatilization amount b of the same at 220° C. is as large as 1,850 mass ppm. The initial fog value in the high temperature and high humidity (H/H) environment after the long period of storage, is as low as 1.0, and the number of sheets for the evaluation of durability is more than 15,000. Therefore, the toner of Comparative Example 2 has no problem with charge stability. Also, the minimum fixing temperature is as low as 155° C. However, since the score of the odor sensory test is as high as 3, the toner of Comparative Example 2 has a problem with odor.

According to Table 1, the toner of Comparative Example 3 is such a toner that the volatilization amount a of the alkylthiol with a molecular weight of 104.2 at 160° C., is 0.51 mass ppm, and the volatilization amount b of the same at 220° C. is as small as 63 mass ppm. The initial fog value in the high temperature and high humidity (H/H) environment after the long period of storage, is as low as 0.9, and the number of sheets for the evaluation of durability is more than 15,000. Therefore, the toner of Comparative Example 3 has no problem with charge stability. Also, the minimum fixing temperature is as low as 160° C. However, since the score of the odor sensory test is as high as 3, the toner of Comparative Example 3 has a problem with odor.

According to Table 1, the toner of Comparative Example 4 is such a toner that the volatilization amount a of the alkylthiol with a molecular weight of 174.4 at 160° C., is 0.31 mass ppm, and the volatilization amount b of the same at 220° C. is as small as 18 mass ppm. The score of the odor sensory test is as low as 1. However, the initial fog value in the high temperature and high humidity (H/H) environment after the long period of storage, is as high as 1.7, and the number of sheets for the evaluation of durability remains at 12,000 sheets. Therefore, the toner of Comparative Example 4 has a problem with charge stability, and the minimum fixing temperature is as high as 170° C.

According to Table 1, the toner of Comparative Example 5 is such a toner that the volatilization amount a of the alkylthiol with a molecular weight of 174.4 at 160° C., is 0.48 mass ppm, and the volatilization amount b of the same at 220° C. is as small as 60 mass ppm. The minimum fixing temperature is as low as 160° C., and the score of the odor sensory test is as low as 1. However, the initial fog value in the high temperature and high humidity (H/H) environment after the long period of storage, is as high as 1.6, and the number of sheets for the evaluation of durability remains at 13,000. Therefore, the toner of Comparative Example 5 has a problem with charge stability.

On the other hand, according to Table 1, the toners of Examples 1 to 5 are such toners that the molecular weight of the alkylthiol is 110 to 150; the volatilization amount a at 160° C. is less than 1 mass ppm; and the volatilization amount b at 220° C. is 30 to 1,000 mass ppm.

According to Table 1, for the toners of Examples 1 to 5, the initial fog value in the high temperature and high humidity (H/H) environment after the long period of storage, is as low as 1.1 or less; the number of sheets for the evaluation of durability is as large as 14,000 or more; the minimum fixing temperature is as low as 155 to 160° C.; and the score of the odor sensory test is 2 or less and excellent.

Therefore, such a toner that the molecular weight of the alkylthiol is 110 to 150; the volatilization amount a at 160° C. is less than 1 mass ppm; and the volatilization amount b at 220° C. is 30 to 1,000 mass ppm, is a toner which can increase charge stability in the high temperature and high humidity environment, which keep odor low, and which is excellent in low-temperature fixability.

REFERENCE SIGNS LIST

1. Evaporator
2. Jacket
3. Agitator furnished with agitating blades
4. Aqueous dispersion of polymer particles
5. Gas intake tube
6. Blower
7. Gas circulation line
8. Condenser
9. Condensation tank
10. Gas circulation line
11. Volatile substance removal device
12. Gas circulation line
13. Gas circulation line
14. Non-contact foam level meter

The invention claimed is:

1. A toner comprising polymer particles obtained by polymerizing a polymerizable monomer and an external additive attached to a surface of the polymer particles,
    wherein a volatilization amount a of an alkylthiol with a molecular weight of 110 or more and less than 150 with respect to the toner, which is quantitated at a volatilization temperature of 160° C. in the following purge & trap/gas chromatography measurement A, is 1 mass ppm or less:
    [purge & trap/gas chromatography measurement A]
        first, 0.1 g of the toner is put in a purge container; with flowing helium gas at 50 mL/min as carrier gas, the purge container is heated from room temperature at a rate of 10° C./min and kept at a temperature of 160° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount a of the alkylthiol with respect to the toner is quantitated by gas chromatography in the following conditions:
    [gas chromatography conditions]
        column temperature: Increased from 50° C. (kept for 2 minutes) to 270° C. (at 10° C./min)
        sample feeding temperature: 280° C.
        detection temperature: 280° C.
        carrier gas: Helium gas (flow rate: 1 mL/min) and
    wherein a volatilization amount b of the alkylthiol with respect to the toner, which is quantitated at a volatilization temperature of 220° C. in the following purge & trap/gas chromatography measurement B, is 30 mass ppm or more and 1,000 mass ppm or less:
    [purge & trap/gas chromatography measurement B]
        first, 0.1 g of the toner is put in a purge container: with flowing helium gas at 50 mL/min as carrier gas, the purge container is heated from room temperature at a rate of 10° C./min and kept at a temperature of 220° C. for 30 minutes; a volatile component thus produced is trapped in a trap tube at −130° C.; and next, with heating the trap tube from −130° C. to 280° C. at a rate of 50° C./min, in which the volatile component is trapped, the volatilization amount b of the alkylthiol with respect to the toner is quantitated by gas chromatography in the following conditions:
    [gas chromatography conditions]
        column temperature: Increased from 50° C. (kept for 2 minutes) to 270° C. (at 10° C./min)
        sample feeding temperature: 280° C.
        detection temperature: 280° C.
        carrier gas: Helium gas (flow rate: 1 mL/min).

2. The toner according to claim 1, wherein a carbon number of an alkyl group in the alkylthiol is 6 or more and 8 or less.

* * * * *